(12) United States Patent
Hebrink et al.

(10) Patent No.: US 10,263,132 B2
(45) Date of Patent: Apr. 16, 2019

(54) SOLAR ENERGY DEVICES

(71) Applicant: 3M INNOVATIVE PROPERTIES COMPANY, St. Paul, MN (US)

(72) Inventors: Timothy J. Hebrink, Scandia, MN (US); Eric R. Jackson, Hastings, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 275 days.

(21) Appl. No.: 14/899,328

(22) PCT Filed: Jun. 25, 2014

(86) PCT No.: PCT/US2014/044006
§ 371 (c)(1),
(2) Date: Dec. 17, 2015

(87) PCT Pub. No.: WO2015/002776
PCT Pub. Date: Jan. 8, 2015

(65) Prior Publication Data
US 2016/0149067 A1 May 26, 2016

Related U.S. Application Data

(60) Provisional application No. 61/841,565, filed on Jul. 1, 2013.

(51) Int. Cl.
*F24S 70/14* (2018.01)
*H01L 31/054* (2014.01)
(Continued)

(52) U.S. Cl.
CPC .......... *H01L 31/0547* (2014.12); *F24S 23/82* (2018.05); *F24S 70/14* (2018.05);
(Continued)

(58) Field of Classification Search
CPC .................................................. H01L 31/0547
See application file for complete search history.

(56) References Cited

U.S. PATENT DOCUMENTS

| | | |
|---|---|---|
| 5,504,134 A | 4/1996 | Palmer |
| 5,552,927 A | 9/1996 | Wheatly |
| (Continued) | | |

FOREIGN PATENT DOCUMENTS

| | | |
|---|---|---|
| JP | H 05-093057 U | 12/1993 |
| JP | 2015-164369 | 9/2015 |
| (Continued) | | |

OTHER PUBLICATIONS

Welford, "The Optics of Nonimaging Concentrators: Light and Solar Energy", Chapter 8, Applications to Solar Energy Concentration, Academic Press, Inc., 1978, pp. 119-141.

(Continued)

*Primary Examiner* — Shannon M Gardner
(74) *Attorney, Agent, or Firm* — Gregory D. Allen

(57) ABSTRACT

Solar energy device (100) comprising at least one of a photovoltaic cell or a solar thermal collector (101) having an absorption bandwidth in the infrared wavelength region of the solar spectrum; a visible light-transmitting reflector (103); and at least one of a graphic film or lighted display (105). The graphic film or a lighted display present is visible through the visible light-transmitting reflector. The solar energy devices can be used, for example, as a sign (e.g., an advertising sign or a traffic sign), on the side and/or roof, as well as in a window, of a building.

8 Claims, 3 Drawing Sheets

(51) Int. Cl.
 *H02S 40/22* (2014.01)
 *G02B 5/08* (2006.01)
 *F24S 20/60* (2018.01)
 *F24S 23/70* (2018.01)
 *F24S 23/77* (2018.01)

(52) U.S. Cl.
 CPC ............ *G02B 5/0841* (2013.01); *H02S 40/22* (2014.12); *F24S 20/60* (2018.05); *F24S 23/77* (2018.05); *Y02B 10/10* (2013.01); *Y02B 10/12* (2013.01); *Y02B 10/20* (2013.01); *Y02E 10/40* (2013.01); *Y02E 10/52* (2013.01)

(56) References Cited

U.S. PATENT DOCUMENTS

| | | | |
|---|---|---|---|
| 5,876,688 | A | 3/1999 | Laundon |
| 5,882,774 | A | 3/1999 | Jonza |
| 6,045,894 | A | 4/2000 | Jonza |
| 6,352,761 | B1 | 3/2002 | Hebrink |
| 6,449,093 | B2 | 9/2002 | Hebrink |
| 6,531,230 | B1 | 3/2003 | Weber |
| 6,783,349 | B2 | 8/2004 | Neavin |
| 6,788,463 | B2 | 9/2004 | Merrill |
| 6,827,886 | B2 | 12/2004 | Neavin |
| 6,830,713 | B2 | 12/2004 | Hebrink |
| 7,141,297 | B2 | 11/2006 | Condo |
| 7,153,588 | B2 | 12/2006 | McMan |
| 7,371,464 | B2 | 5/2008 | Sherman |
| 2006/0084780 | A1 | 4/2006 | Hebrink |
| 2007/0148474 | A1 | 6/2007 | Leir |
| 2007/0177272 | A1 | 8/2007 | Benson |
| 2009/0126777 | A1 | 5/2009 | Khazeni |
| 2010/0075136 | A1 | 3/2010 | Song |
| 2010/0096006 | A1 | 4/2010 | Griffiths |
| 2010/0096011 | A1 | 4/2010 | Griffiths |
| 2011/0123800 | A1 | 5/2011 | Sherman |
| 2014/0290723 | A1 | 10/2014 | Gilbert |
| 2014/0299175 | A1 | 10/2014 | Gilbert |

FOREIGN PATENT DOCUMENTS

| | | |
|---|---|---|
| WO | WO 2009/063822 | 5/2009 |
| WO | WO 2009/140493 | 11/2009 |
| WO | WO 2010/078105 | 7/2010 |
| WO | WO 2010/078289 | 7/2010 |
| WO | WO 2011/062836 | 5/2011 |
| WO | WO 2012/047867 | 4/2012 |
| WO | WO 2012/047877 | 4/2012 |
| WO | WO 2012/058086 | 5/2012 |
| WO | WO 2012/058090 | 5/2012 |
| WO | WO 2012/154793 | 11/2012 |
| WO | WO 2012/154803 | 11/2012 |
| WO | WO 2013/019766 | 2/2013 |
| WO | WO 2013/142239 | 9/2013 |
| WO | WO 2014/022049 | 2/2014 |
| WO | WO 2014/099367 | 6/2014 |
| WO | WO 2014/193550 | 12/2014 |

OTHER PUBLICATIONS

International Search Report for PCT International Application No. PCT/US2014/044006 dated Sep. 26, 2014, 5 pages.

SOLAR ENERGY DEVICES

CROSS REFERENCE TO RELATED APPLICATIONS

This application is a national stage filing under 35 U.S.C. 371 of PCT/US2014/044006, filed Jun. 25, 2014, which claims priority to U.S. Provisional Application No. 61/841,565, filed Jul. 1, 2013, the disclosure of which is incorporated by reference in its/their entirety herein.

BACKGROUND

It is known to install and/or integrate photovoltaic devices and systems into commercial and residential buildings. Such systems have generally been limited to conventional rooftop based systems that may have limited photovoltaic capability and little aesthetic appeal. Conventional roof-top based systems typically depend on racking systems, which typically are not suitable, for example, for integrating into a vertical building face in an attractive and convenient manner and may have limited suitability in other configurations also.

In concentrated photovoltaic applications, conventional solar concentrating mirrors are typically used to direct broad bandwidths of solar energy onto a photovoltaic cell or solar heat transfer element. However, electromagnetic radiation of certain wavelengths reflected from the solar concentrating mirror onto the solar element may adversely affect the solar element. For example, certain wavelengths in the infrared spectrum can cause certain photovoltaic cells to undesirably increase in temperature. As a result, the photovoltaic cells may lose efficiency and degrade over time due the excessive thermal exposure. In addition, broadband mirrors which reflect visible light can be blinding at certain angles, and objectionable to some for aesthetic reasons. Broadband mirrors are also used in concentrating solar thermal panels to heat fluids, but again lack aesthetic appeal for building integration, and stray reflections can be blinding in systems that do not track the sun. Long term exposure to ultraviolet (UV) light also typically leads to premature degradation of components of the photovoltaic cell. Some solar concentrating mirrors that reflect wavelengths corresponding to the absorption bandwidth of a selected solar cell and either transmits or absorbs a major portion of light outside this bandwidth have been disclosed (see, e.g., Int. Pat. App. Pub. No. WO 2009/140493 (Hebrink et al.), published Nov. 19, 2009).

SUMMARY

In one aspect, the present disclosure describes a solar energy device comprising:
  at least one of a photovoltaic cell or a solar thermal collector having an absorption bandwidth that includes at least a portion (e.g., at least in a 100 nm range; in some embodiments, at least in a 200 nm, 300 nm, 400 nm, 500 nm, 600 nm, 700 nm, 800 nm, 900 nm, or even at least 1000 nm range) of the near infrared wavelength region of the solar spectrum (i.e., at least a portion in a range from 800 nm to 1200 nm);
  a visible light-transmitting reflector having first and second generally opposed major surfaces, the visible light-transmitting reflector positioned to reflect light from the first major surface onto the at least one of a photovoltaic cell or a solar thermal collector, the visible light-transmitting reflector comprising a multilayer optical film having an optical stack comprising a plurality of alternating first and second optical layers with different indices of refraction, wherein the multilayer optical film reflects at least a portion of light in a range of wavelengths that corresponds with the absorption bandwidth of the at least one of a photovoltaic cell or a solar thermal collector; and
  at least one of a graphic film (in some embodiments, a partially transmissive graphic film) or lighted display (e.g., a liquid crystal display) positioned closer to the second major surface of the visible light-transmitting reflector than to the first major surface of the visible light-transmitting reflector, wherein the graphic film or lighted display present is visible through the visible light-transmitting reflector.

In another aspect, the present disclosure describes a solar energy device comprising:
  at least one of a photovoltaic cell or a solar thermal collector having an absorption bandwidth that includes at least a portion of the near infrared wavelength region of the solar spectrum (i.e., at least a portion in a range from 800 nm to 1200 nm);
  a visible light-transmitting reflector having first and second generally opposed major surfaces, the visible light-transmitting reflector positioned to reflect light from the first major surface onto the at least one of a photovoltaic cell or a solar thermal collector, the visible light-transmitting reflector comprising a multilayer optical film having an optical stack comprising a plurality of alternating first and second optical layers with different indices of refraction, wherein the multilayer optical film reflects at least a portion of light in a range of wavelengths that corresponds with the absorption bandwidth of the at least one of a photovoltaic cell or a solar thermal collector; and
  a partially transmissive graphic film positioned closer to the first major surface of the visible light-transmitting reflector than to the second major surface of the visible light-transmitting reflector, wherein reflected infrared light transmits through the partially transmissive graphic film.

A "graphic film" is any film that absorbs at least some light having wavelengths in the visible or near infrared range and that reflects at least some light in the visible range where the reflected light contains some graphical content. The graphical content may include patterns, images or other visual indicia. The graphic film may be a printed film or the graphic may be created by means other than printing. For example, the graphic film may be perforated reflective film with a patterned arrangement of perforations. The graphic may also be created by embossing. In some embodiments, the graphic film is a partially transmissive graphic film (e.g., in use in a backlighted sign (e.g., a backlighted, traffic sign)). Examples of commercially available graphic films are marketed under the trade designation "DI-NOC" by 3M Company, St. Paul, Minn.

A "photovoltaic cell" is a semi-conductor electrical device that converts electromagnetic energy (e.g., light, including near infrared) into electricity.

A "solar thermal collector" is a device that can convert electromagnetic energy from the sun (i.e., sunlight, including infrared energy) into thermal energy.

A "solar energy device" is a device that can convert electromagnetic energy from the sun (i.e., sunlight, including infrared energy) into electricity or thermal energy for use elsewhere.

The term "polymer" refers to a macromolecular compound consisting essentially of one or more repeated monomeric units, or a mixture of macromolecular compounds that consist essentially of one or more like repeated monomeric units.

Solar energy devices described herein can be used, for example, as signs (e.g., an advertising sign or a traffic sign), on the side and/or roof, as well as in a window, of a building The solar energy device may be installed, for example, as part of a building and allow visibility of the graphic film or lighted display positioned closer to the second major surface of the visible light transmitting reflector. The graphic film may have the printed appearance, for example, of shingles, tiles, bricks, stucco, or wood grain for building aesthetics.

DETAILED DESCRIPTION

Figure 1:
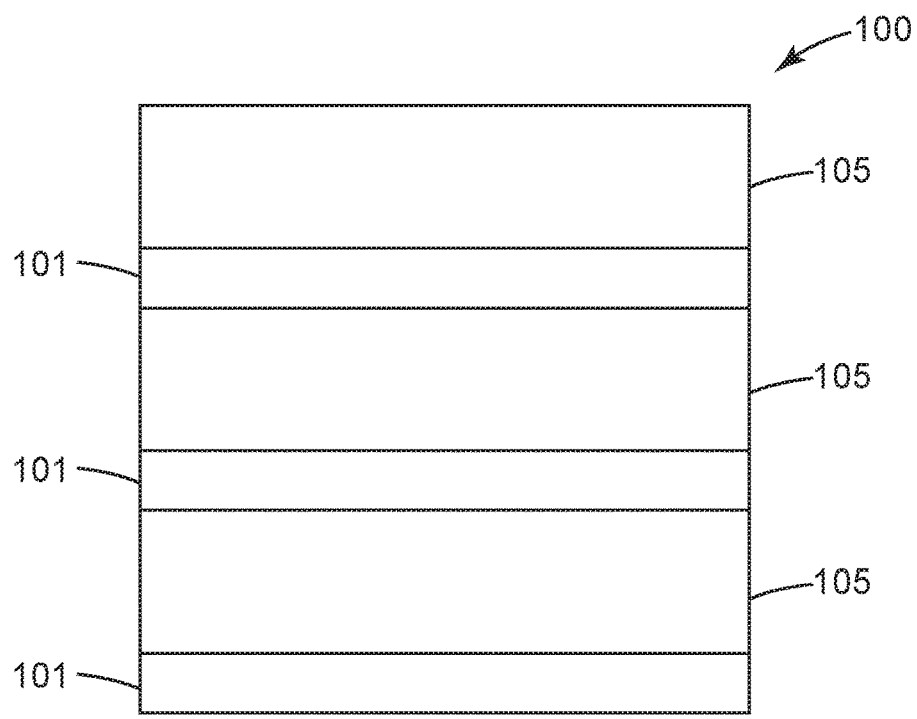
FIG. 1 is a schematic front view of an exemplary embodiment of a solar energy device described herein.
Figure 1A:
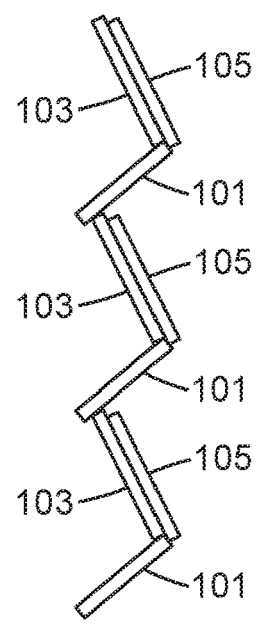
FIG. 1A is a schematic side view of the exemplary embodiment solar energy device shown in FIG. 1.

Referring to FIGS. 1 and 1A, solar energy device 100 comprises photovoltaic cell or solar thermal collector 101, visible light-transmitting reflector 103, and graphic film or lighted display 105.

Figure 2:
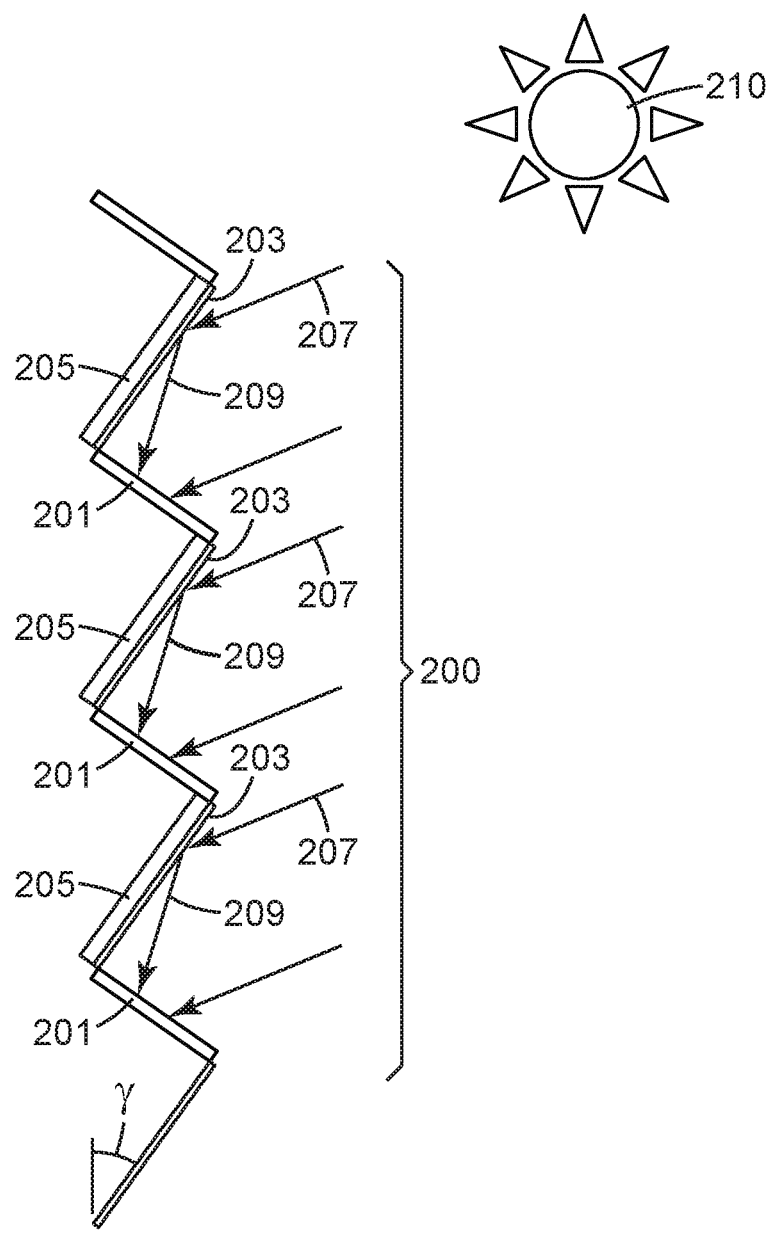
FIG. 2 is a schematic side view of an exemplary embodiment of a solar energy device described herein in use.

Referring to FIGS. 2, solar energy device 200 comprises photovoltaic cell or solar thermal collector 201, visible light-transmitting reflector 203, and graphic film or lighted display 205. Incident sunlight 207 from sun 210 irradiates directly onto photovoltaic cells or solar thermal collector 201 and visible light transmitting reflectors 203. Near infrared portion of energy 209 from sun 210 is reflected from visible light-transmitting reflectors 203 onto photovoltaic cell or solar thermal collector 201. Graphic film or lighted display 205 is viewable through visible light-transmitting reflector 203.

Figure 3:
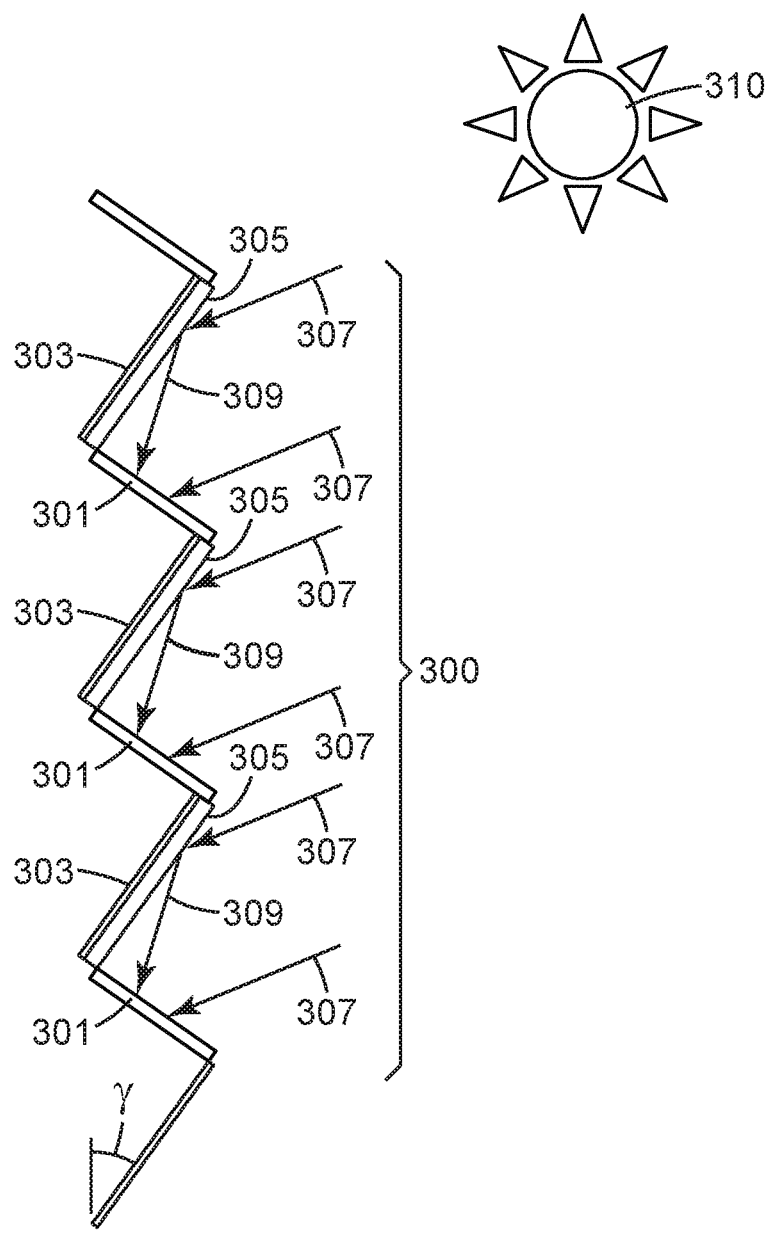
FIG. 3 is a schematic side view of an exemplary embodiment of a solar energy device described herein in use.

Referring to FIG. 3, solar energy device 300 comprises photovoltaic cell or solar thermal collector 301, visible light-transmitting reflector 303, and partially transmissive graphic film or lighted display 305. Incident sunlight 307 from sun 310 irradiates onto photovoltaic cells or solar thermal collector 301 and visible light transmitting reflectors 303 through partially transmissive graphic or lighted display 305. Near infrared portion of energy 309 from sun 310 is reflected from visible light-transmitting reflectors 303 through partially transmissive graphic or lighted display 305 onto photovoltaic cell or solar thermal collector 301.

Exemplary photovoltaic cells include a crystalline silicon single junction cell, a ribbon silicon cell, an amorphous silicon photovoltaic cell, a copper indium gallium selenide cell, a cadmium telluride photovoltaic cell, an organic photovoltaic cell, and a gallium arsenide cell.

Exemplary solar thermal collectors include glazed flat black panels, black water tubes attached to black solar absorbing fins, and evacuated glass tubes surrounding absorber tubes, compound parabolic concentrators reflecting additional infrared light onto solar absorbing tubes.

Solar energy devices described herein include a visible light-transmitting reflector that comprises a multilayer optical film having an optical stack with a plurality of alternating first and second optical layers with different indices of refraction. Conventional multilayer optical films with alternating layers of at least one first polymer and one second polymer may be employed in creating the visible light-transmitting reflector. By selecting the appropriate layer pairs with appropriate refractive indices, the layer thickness, and/or the number of layer pairs, the optical stack can be designed to transmit or reflect desired wavelengths of light.

By appropriate selection of the first optical layers and the second optical layers, the visible light transmitting reflector in the solar energy device disclosed herein can be designed to reflect or transmit a desired bandwidth of light. Reflection is generated at each interface between optical layers in an optical stack, which layers have refractive indices that are different, $n_1$ and $n_2$, respectively. Light that is not reflected at the interface of adjacent optical layers typically passes through successive layers and is either absorbed in a subsequent optical layer, reflected at a subsequent interface, or is transmitted through the optical stack altogether. Typically, the optical layers of a given layer pair are selected such as to be substantially transparent to those light wavelengths at which reflectivity is desired. Light that is not reflected at a layer pair interface passes to the next layer pair interface where a portion of the light is reflected and unreflected light continues on, and so on. Increasing the number of optical layers in the optical stack may provide more optical power. In this way, an optical layer stack with many optical layers is capable of generating a high degree of reflectivity. For example, if the refractive index between the layer pairs is small, the optical stack may not achieve the desired reflectivity, however by increasing the number of layer pairs, sufficient reflectivity may be achieved. In some embodiments of the present disclosure, the optical stack comprises at least 2 first optical layers and at least 2 second optical layers, at least 5 first optical layers and at least 5 second optical layers, at least 50 first optical layers and at least 50 second optical layers, at least 200 first optical layers and at least 200 second optical layers, at least 500 first optical layers and at least 500 second optical layers, or at least 1000 first optical layers and at least 1000 second optical layers. In general, at least a portion of the first optical layers and at least a portion of the second optical layers are in intimate contact.

In general, the reflectivity of the interface of adjacent optical layers is proportional to the square of the difference in index of refraction of the first optical layer and the second optical layer at the reflecting wavelength. The absolute difference in refractive index between the layer pair $(n_1-n_2)$ is typically 0.1 or larger. Higher refractive index differences between the first optical layer and the second optical layer are useful, for example, for providing higher optical power (e.g., reflectivity), which enables more reflective bandwidth. However, in the present disclosure, the absolute difference between the layer pair may be less than 0.20 (in some embodiments, less than 0.15, 0.10, 0.05, or even less than 0.03), depending on the layer pair selected.

The thickness of each layer may influence the performance of the optical stack by either changing the amount of reflectivity or shifting the reflectivity wavelength range. The optical layers typically have an average individual layer thickness of about one quarter of the wavelength or wavelengths to be reflected, and a layer pair thickness of about one half of the wavelength or wavelengths to be reflected. The optical layers can each be a quarter-wavelength thick or the optical layers can have different optical thicknesses, as long as the sum of the optical thicknesses for the layer pair is half of a wavelength (or a multiple thereof). For example, to reflect 800 nanometers (nm) light, the average individual layer thickness would be about 200 nm, and the average layer pair thickness would be about 400 nm. First optical layers and second optical layers may have the same thicknesses. Alternatively, the optical stack can include optical layers with different thicknesses to increase the reflective wavelength range. An optical stack having more than two layer pairs can include optical layers with different optical thicknesses to provide reflectivity over a range of wavelengths. For example, an optical stack can include layer pairs that are individually tuned to achieve optimal reflection of normally incident light having particular wavelengths or may include a gradient of layer pair thicknesses to reflect light over a larger bandwidth. The normal reflectivity for a particular layer pair is primarily dependent on the optical thickness of the individual layers, where optical thickness is defined as the product of the actual thickness of the layer times its refractive index. The intensity of light reflected from the optical layer stack is a function of its number of layer pairs and the differences in refractive indices of optical layers in each layer pair. The ratio $n_1d_1/(n_1d_1+n_2d_2)$ (commonly termed the "f-ratio") correlates with reflectivity of a given layer pair at a specified wavelength. In the f-ratio, $n_1$ and $n_2$ are the respective refractive indices at the specified wavelength of the first and second optical layers in a layer pair, and $d_1$ and $d_2$ are the respective thicknesses of the first and second optical layers in the layer pair. By proper selection of the refractive indices, optical layer thicknesses, and f-ratio, one can exercise some degree of control over the intensity of first order reflection.

The equation $\lambda/2=n_1d_1+n_2d_2$ can be used to tune the optical layers to reflect light of wavelength $\lambda$ at a normal angle of incidence. At other angles, the optical thickness of the layer pair depends on the distance traveled through the component optical layers (which is larger than the thickness of the layers) and the indices of refraction for at least two of the three optical axes of the optical layer.

The optical stack in the multilayer optical film useful for the visible light-transmitting reflector disclosed herein typically includes all or mostly quarter-wave film stacks. In this case, control of the spectrum requires control of the layer thickness profile in the film stack. Layer thickness profiles of such optical stacks can be adjusted to provide for improved spectral characteristics using the axial rod apparatus taught, for example, in U.S. Pat. No. 6,783,349 (Neavin et al.) combined with layer profile information obtained with microscopic techniques.

The basic process for layer thickness profile control involves adjustment of axial rod zone power settings based on the difference of the target layer thickness profile and the measured layer profile. The axial rod power increase needed to adjust the layer thickness values in a given feedblock zone may first be calibrated in terms of watts of heat input per nanometer of resulting thickness change of the layers generated in that heater zone. Fine control of the spectrum is possible using 24 axial rod zones for 275 layers. Once calibrated, the necessary power adjustments can be calculated once given a target profile and a measured profile. The procedure may be repeated until the two profiles converge.

Desirable techniques for providing a multilayer optical film with a controlled spectrum include the use of an axial rod heater control of the layer thickness values of coextruded polymer layers as taught, for example, in U.S. Pat. No. 6,783,349 (Neavin et al.); timely layer thickness profile feedback during production from a layer thickness measurement tool (e.g., an atomic force microscope, a transmission electron microscope, or a scanning electron microscope); optical modeling to generate the desired layer thickness profile; and making axial rod adjustments based on the difference between the measured layer profile and the desired layer profile.

The layer thickness profile (layer thickness values) of the optical stack may be adjusted to be approximately a linear profile with the first (thinnest) optical layers adjusted to have about a quarter wave optical thickness (index times physical thickness) for the left band edge of the desired reflection bandwidth and progressing to the thickest layers, which may be adjusted to be about a quarter wave thick optical thickness for the right band edge of the desired reflection bandwidth. In some embodiments, two or more multilayer optical films with different reflection bands are laminated together to broaden the reflection band.

Birefringence (e.g., caused by stretching) of optical layers may increase the difference in refractive index of the optical layers in a layer pair. Optical stacks that include layer pairs, which are oriented in two mutually perpendicular in-plane axes are highly efficient reflectors that capable of reflecting an extraordinarily high percentage of incident light depending on, for example, the number of optical layers, f-ratio, and the indices of refraction.

The reflector in the solar energy device disclosed herein transmits visible light. That is, at least a portion of the wavelengths in a range from 400 to 700 nanometers is transmitted. "At least a portion" is meant to comprise not only the entire range of wavelengths between 400 and 700 nanometers, but also a portion of the wavelengths, such as a bandwidth of at least 25 nm (in some embodiments, at least 50 nm, 100 nm, 150 nm, or at least 200 nm. In these embodiments, the transmission may be measured at a normal angle to the multilayer optical film or at a shifted angle of 45 to 60 degrees. In some embodiments, the multilayer optical film has an average visible light transmission of at least 45 (in some embodiments, at least 50, 60, 70, 80, 85, 90, 92, or even at least 95) percent at an angle normal to the multilayer optical film. In some embodiments, the multilayer optical film has an average visible light transmission of at least 45 (in some embodiments, at least 50, 60, 70, 80, 85, 90, 92, or even at least 95) percent in a wavelength range selected from the group consisting of 400 nanometers to 500 nanometers, 400 nanometers to 600 nanometers, and 400 nanometers to 700 nanometers at a 0 degree angle of incidence (i.e., an angle normal to the film).

In many solar energy device constructions (e.g., conventional roof-top devices) transmission to visible light is unnecessary. For example, solar backsheets or reflectors on roof tops are often formed on opaque substrates. In some applications, including concentrated photovoltaic applications, it may be considered desirable for a reflector (concentrating mirror) to reflect most of the light usable by photovoltaic cells, which tend to absorb light in the visible range. For example, Int. Pat. App. Pub. No. 2009/140493 (Hebrink et al.) discloses a multilayer film, useful as a solar concentrating mirror, that reflects at least a major portion of the average light across the range of wavelengths that corresponds with the absorption bandwidth of the solar cell onto the solar cell. In contrast, the reflectors of the present disclosure reflect wavelengths in a range that are absorbed by photovoltaic cells or a solar thermal collector and also transmit visible light that is useful, for example, for viewing of a display, viewing of an existing building façade, or viewing of graphics designed to look like a building façade.

The multilayer optical film in the visible light-transmitting reflector disclosed herein may be designed to switch from transmitting to reflecting in the visible range (e.g., in a range from 600 nanometers to 700 nanometers) or in the infrared range (e.g., in a range from 700 nanometers to 900 nanometers). In some embodiments, the visible light-transmitting reflector has an average visible light transmission of at least 30 percent. The wavelength at which the film switches from transmitting to reflecting visible light is called the left band edge. In some embodiments, the multilayer optical film is a visible light transmitting reflector having a left band edge in a range from 600 nanometers to 1000 nanometers. In some embodiments, the multilayer optical film has an average light reflection of at least 50 percent at a normal angle to the multilayer optical film in a wavelength range selected from the group consisting of 650 nanometers to 1350 nanometers, 650 nanometers to 1500 nanometers, 850 nanometers to 1200 nanometers, and 850 nanometers to 1500 nanometers. In some embodiments, the multilayer optical film is a color-shifting film. Color-shifting films change color as a function of viewing angle. For example, if the left band edge of the multilayer optical film is about 650 nanometers, against a white background, the film may appear cyan at a zero degree viewing angle and cobalt blue at a shifted viewing angle of 45 degrees to 60 degrees. In another example, if the left band edge of the multilayer optical film is about 720 nanometers, against a white background, the film may appear colorless at a zero degree viewing angle and cyan at a shifted viewing angle of 45 degrees to 60 degrees. For narrow transmission bands (that is, transmission bands in a range of about 100 nanometers or less), many colors may be seen at successively higher angles of incidence. Further details about color-shifting films may be found, for example, in U.S. Pat. No. 6,531,230 (Weber et al.) and U.S. Pat. No. 6,045,894 (Jonza et al).

In the solar energy devices described herein, the visible light-transmitting reflector reflects at least a portion of the light in a range of wavelengths that corresponds with the absorption bandwidth of the photovoltaic cell or solar thermal collector. "At least a portion" includes bandwidths such as at least 25 nm (in some embodiments, at least 50 nm, 100 nm, 150 nm or even at least 200 nm).

Suitable photovoltaic cells include those that have been developed with a variety of semiconductor materials. Each type of semiconductor material will have a characteristic band gap energy which causes it to absorb light most efficiently at certain wavelengths of light, or more precisely, to absorb electromagnetic radiation over a portion of the solar spectrum. Exemplary suitable materials useful for making photovoltaic cells and their photovoltaic light absorption band-edge wavelengths include: a crystalline silicon single junction (about 400 nm to about 1150 nm), amorphous silicon single junction (about 300 nm to about 720 nm), ribbon silicon (about 350 nm to about 1150 nm), copper indium gallium selenide (CIGS) (about 350 nm to about 1100 nm), cadmium telluride (CdTe) (about 400 nm to about 895 nm), and gallium arsenide (GaAs) multi-junction (about 350 nm to about 1750 nm).

The photovoltaic cell may also be a bifacial cell or a dye-sensitized cell. In some embodiments, the photovoltaic cell is a crystalline silicon single junction cell, a ribbon silicon cell, a CIGS cell, a GaAs multi-junction cell, or a CdTe cell. In some embodiments, the photovoltaic cell is a crystalline silicon single junction cell, a ribbon silicon cell, a CIGS cell, or a GaAs cell. In some embodiments, the photovoltaic cell is a crystalline silicon single junction cell. New materials suitable for making photovoltaic cells continue to be developed. In some embodiments, the photovoltaic cell is an organic photovoltaic cell. In some of these embodiments, the organic photovoltaic cell is transparent, which may be beneficial to the aesthetic function for the solar energy devices described herein.

Suitable solar thermal collectors include glazed flat black panels, black fluid containing tubes attached to black solar absorbing fins, evacuated glass tubes surrounding absorber tubes, truncated compound parabolic concentrators reflecting solar energy onto solar absorbing tubes (such as those described in "The Optics of Non-imaging Concentrators Light and Solar Energy" written by W. T. Welford and R. Winston and published by Academic Press in 1978), and parabolic concentrators with infrared mirrors that track the sun. Thermal heat collected by the fluid can be employed for hot tap water, building heat, heat powered air conditioning (adsorption cooling), dehumidification of air, and process heat.

Typically, the visible light transmitting mirrors in the solar energy devices described herein, reflect at least a portion of the light in a range of wavelengths that corresponds with the absorption bandwidth of the photovoltaic cell including near infrared wavelengths and optionally longer visible wavelengths of light. In some embodiments, the visible light-transmitting reflector according to the present disclosure reflects light in at least a portion of the wavelength range of 650 nm to 1100 nm (in some embodiments, 650 nm to 1500 nm, 875 nm to 1100 nm, or even 900 nm to 1500 nm). For any of these wavelength ranges, the visible light-transmitting reflector may have an average reflection of at least 30 (in some embodiments, at least 40, 50, 60, 70, 80, 90, 95, 97, 98, or even at least 99) percent at a normal angle of incidence. The visible light-transmitting reflector is positioned to reflect the desired bandwidth of light onto the photovoltaic cell or solar thermal collector. In some embodiments, light outside the range of wavelengths that corresponds with the absorption bandwidth of the photovoltaic cell or solar thermal collector passes through the visible light-transmitting reflector and is not reflected onto the photovoltaic cell or solar thermal collector. In other embodiments, some of the light outside the range of wavelengths that corresponds with the absorption bandwidth of the photovoltaic cell or solar thermal collector is absorbed by the visible light-transmitting reflector, as described below. The selection of multilayer optical films that reflect at least a portion of light in a range of wavelengths that matches selected photovoltaic cells or solar thermal collectors, while reducing radiation adverse to the photovoltaic cell or solar thermal collector, can significantly enhance the operational efficiency of the photovoltaic cell or solar thermal collector.

The visible light-transmitting reflector disclosed herein includes first and second optical layers having different indices of refraction. Typically, the first and second optical layers are polymer layers. In this context, the term "polymer" will be understood to include homopolymers and copolymers, as well as polymers or copolymers that may be formed in a miscible blend, for example, by co-extrusion or by reaction, including transesterification. The terms "polymer" and "copolymer" include both random and block copolymers. The polymer in the first optical layer described herein has a higher refractive index than the polymer in the second optical layer. Useful classes of polymers for first optical layers include, in some embodiments, polyesters and polycarbonates.

Polyesters may be derived, for example, from ring-opening addition polymerization of a lactone, or by condensation of a dicarboxylic acid (or derivative thereof (e.g., a diacid halide or a diester) with a diol). Exemplary dicarboxylic acids include 2,6-naphthalenedicarboxylic acid; terephthalic acid; isophthalic acid; phthalic acid; azelaic acid; adipic acid; sebacic acid; norbornenedicarboxylic acid; bicyclooctanedicarboxylic acid; 1,6-cyclohexanedicarboxylic acid; t-butyl isophthalic acid; trimellitic acid; sodium sulfonated isophthalic acid; 4,4'-biphenyldicarboxylic acid. Acid halides and lower alkyl esters of these acids (e.g., methyl or ethyl esters) may also be used as functional equivalents. The term "lower alkyl" refers, in this context, to alkyl groups having from one to four carbon atoms. Exemplary diols include ethylene glycol; propylene glycol; 1,4-butanediol; 1,6-hexanediol; neopentyl glycol; polyethylene glycol; diethylene glycol; tricyclodecanediol; 1,4-cyclohexanedimethanol; norbornanediol; bicyclooctanediol; trimethylolpropane; pentaerythritol; 1,4-benzenedimethanol; bisphenol A; 1,8-dihydroxybiphenyl; and 1,3-bis (2-hydroxyethoxy) benzene.

In some embodiments, the first optical layer comprises a birefringent polymer. Exemplary polymers useful for forming birefringent optical layers include polyethylene terephthalates (PETs); polyethylene 2,6-naphthalates (PENs); copolyesters derived from naphthalenedicarboxylic acid, an additional dicarboxylic acid, and a diol (coPENs) (e.g., a polyester derived through co-condensation of 90 equivalents of dimethyl naphthalenedicarboxylate, 10 equivalents of dimethyl terephthalate, and 100 equivalents of ethylene glycol); copolyesters derived from terephthalic acid such as those described in U.S. Pat. No. 6,449,093 B2 (Hebrink et al.) or U.S. Pat. App. Publ. No. 2006/0084780 A1 (Hebrink et al.); copolymers of PEN (CoPEN) such as those described in U.S. Pat. No. 6,352,761 (Hebrink et al.) and U.S. Pat. No. 6,449,093 (Hebrink et al.); polyether imides; polyester/non-polyester combinations; polybutylene 2,6-naphthalates (PBNs); modified polyolefin elastomers, thermoplastic elastomers; thermoplastic polyurethanes (TPUs); and syndiotactic polystyrenes (sPSs), which are useful, for example, for their low UV-light absorbance; and combinations thereof.

In some embodiments, the first optical layer comprises an acrylic (e.g., poly(methyl methacrylate) PMMA)), a polycarbonate, a polyolefin copolymer (e.g.,(EVA) ethylene vinyl acetate), a cyclic olefin copolymer, or a combination thereof. Such embodiments may be useful, for example, when the second optical layer comprises a fluoropolymer.

Exemplary specific polymer products that may be useful for the first optical layers include a PET having an inherent viscosity of 0.74 dL/g, available, for example, from Eastman Chemical Company, Kingsport, Tenn., and PMMA available, for example, under the trade designations "CP71" and "CP80" from Ineos Acrylics, Inc., Wilmington, Del.

The second optical layers of the multilayer optical film can be made, for example, from a variety of polymers. The polymer in the second optical layer may have a glass transition temperature compatible with that of the polymer in the first optical layer. In some embodiments, the polymer in the second optical layer has a refractive index similar to the isotropic refractive index of a birefringent polymer useful for making the first optical layers. Exemplary melt-processible polymers useful in the second optical layers include: polyesters (e.g., polycyclohexanedimethylene terephthalate commercially available, for example, from Eastman Chemical Co, Kingsport, Tenn.); polysulfones; polyurethanes; polyamides; polyimides; polycarbonates; polydimethylsiloxanes; polydiorganosiloxane polyoxamide block copolymers (OTPs) such as those described in U.S. Pat. Appln. Publ. Nos. 2007/0148474 A1 (Leir et al.) and 2007/0177272 A1 (Benson et al.); fluoropolymers including homopolymers such as polyvinylidene difluoride (PVDFs), copolymers (e.g., copolymers of tetrafluoroethylene, hexafluoropropylene, and vinylidene fluoride (THVs), copolymers of hexafluoropropylene, tetrafluoroethylene, and ethylene (HTEs); copolymers of tetrafluoroethylene and norbornene; copolymers of ethylene and tetrafluoroethylene (ETFEs); copolymers of ethylene and vinyl acetate (EVAs); copolymers of ethylene and chlorotrifluoroethylene (ECTFEs)), fluoroelastomers; acrylics (e.g., PMMA (available, for example, under the trade designations "CP71" and "CP80" from Ineos Acrylics)) and copolymers of methyl methacrylate (coPMMAs) (e.g., a coPMMA made from 75 weight percent methyl methacrylate and 25 weight percent ethyl acrylate (available, for example, from Ineos Acrylics, Inc., under trade designations "PERSPEX CP63" and a coPMMA formed from methyl methacrylate and n-butyl methacrylate); styrenic polymers; vinyl acetate copolymers (e.g., ethylene vinyl acetate copolymers); copolymers of ethylene and a cyclic olefin (COCs); blend of PMMA and PVDF (available, for example, from Solvay Polymers, Inc., Houston, Tex., under the trade designation "SOLEF"); polyolefin copolymers such as poly (ethylene-co-octene) (PEPOs) available, for example, from Dow Chemical Co., Midland, Mich., under the trade designation "ENGAGE 8200", poly (propylene-co-ethylene) (PPPE) available, for example, from Fina Oil and Chemical Co., Dallas, Tex. under the trade designation "Z9470," and a copolymer of atactic polypropylene (aPPs) and isotactic polypropylene (iPPs) available, for example, from Huntsman Chemical Corp., Salt Lake City, Utah under the trade designation "REXFLEX W111"; and combinations thereof. Second optical layers can also be made from a functionalized polyolefin such as linear low density polyethylene-g-maleic anhydride (LLDPE-g-MA) (available, for example, from E. I. du Pont de Nemours & Co., Inc., Wilmington, Del. under the trade designation "BYNEL 4105") or blends of this polymer and others described above.

In some embodiments, polymer compositions suitable for the second optical layers include PMMA, CoPMMA, polydimethyl siloxane oxamide based segmented copolymer (SPDX), fluoropolymers including homopolymers such as PVDF and copolymers such as those derived from tetrafluoroethylene, hexafluoropropylene, and vinylidene fluoride (THVs), blends of PVDF and PMMA, acrylate copolymers, styrene, styrene copolymers, silicone copolymers, polycarbonate, polycarbonate copolymers, polycarbonate blends, blends of polycarbonate and styrene maleic anhydride, and cyclic-olefin copolymers. In some embodiments, the second optical layers comprise poly(methyl methacrylate), copolymers of methyl methacrylate and other acrylate monomers, or blends of poly(methyl methacrylate) and poly(vinylidene difluoride).

The selection of the polymer compositions used in creating the multilayer optical film will depend upon the desired bandwidth that will be reflected onto a chosen photovoltaic cell or solar thermal collector. Higher refractive index differences between the polymers in the first and the second optical layers create more optical power thus enabling more reflective bandwidth. Alternatively, additional layers may be employed to provide more optical power. Exemplary useful combinations of first and second polymer layers include polyethylene terephthalate with copolymers of tetrafluoroethylene, hexafluoropropylene, and vinylidene fluoride; polyethylene terephthalate with polydimethyl siloxane oxamide based segmented copolymer, polyethylene terephthalate with poly(methyl methacrylate); polyethylene terephthalate with a polyvinylidene difluoride and poly(methyl methacrylate) blend; polyethylene 2,6-naphthalate with copolymers of tetrafluoroethylene, hexafluoropropylene, and vinylidene fluoride; polyethylene 2,6-naphthalate with polydimethyl siloxane oxamide based segmented copolymer; polyethylene 2,6-naphthalate with poly(methyl methacrylate); polyethylene terephthalate with copolymers of methyl methacrylate; polyethylene 2,6-naphthalate with copolymers of methyl methacrylate; copolymers of polyethylene 2,6-naphthalate with poly(methyl methacrylate); copolymers of polyethylene 2,6-naphthalate with polydimethyl siloxane oxamide based segmented copolymer; syndiotactic polystyrene with polydimethyl siloxane oxamide based segmented copolymer; syndiotactic polystyrene with copolymers of tetrafluoroethylene, hexafluoropropylene, and vinylidene fluoride; copolymers of polyethylene 2,6-naphthalate with copolymers of tetrafluoroethylene, hexafluoropropylene, and vinylidene fluoride; polyethylene terephthalate with fluoroelastomers; syndiotactic polystyrene with fluoroelastomers; copolymers of polyethylene 2,6-naphthalate with fluoroelastomers; and poly(methyl methacrylate) with copolymers of tetrafluoroethylene, hexafluoropropylene, and vinylidene fluoride.

In some embodiments, the optical layers comprise inorganic materials. These materials can be, for example, thin film vacuum vapor deposited (e.g., by chemical vapor deposition, sputtering, or physical vapor deposition). Suitable high refractive index materials include titanium oxide ($TiO_2$), cerium oxide ($CeO_2$), zirconia ($ZrO_2$), and tantalum oxide ($Ta_2O_5$), or even niobia ($Nb_2O_5$) and hafnia ($HfO_2$). Suitable low refractive index materials include silicon dioxide ($SiO_2$), silicon sesquioxide and aluminum oxide ($Al_2O_3$), and even magnesium fluoride ($MgF_2$).

In some embodiments, the optical layers could also comprise mixtures of the inorganic materials above and organic binders. In one embodiment, the optical layers comprise polyelectrolyte solutions of polymer-inorganic nanoparticle layers. For example, the plurality of optical layers could be deposited by a layer-by-layer self-assembly coating method as described in co-pending patent application having Ser. No. 61/829,332, filed May 31, 2013) and 61/740,165, filed Dec. 20, 2012. Further details relating to the selection of materials and manufacturing of optical stacks and multilayer optical films are described, for example, in U.S. Pat. No. 5,552,927 (Wheatley et al.); U.S. Pat. No. 5,882,774 (Jonza et al.); U.S. Pat. No. 6,827,886 (Neavin et al.); U.S. Pat. No. 6,830,713 (Hebrink et al.); and U.S. Pat. No. 7,141,297 (Condo et. al.); and in Int. Pat. App. Pub. No. WO 2010/078289 (Hebrink et al.).

Exemplary lighted displays include liquid crystal displays and backlit signs which can be illuminated with fluorescent bulbs, light emitting diodes, and other light sources.

In some embodiments, the graphic film includes a graphic covering at least about 75% (in some embodiments, at least about 70%, 65%, 55%, 50%, 45%, 40%, 35%, 30%, 25%, 20%, 15%, 10%, or even at least about 5%) of the second surface of the infrared mirror.

The graphic film may be perforated film that is printable or otherwise imageable. A film is printable if it is capable of receiving an ink image. Useful perforated printable films include, for example, perforated clear vinyl films available from, for example, under the trade designation "SCOTCHCAL MARKING FILM" from 3M Company, St. Paul, Minn. In some embodiments, the graphic film may comprise a thermoplastic urethane and a cellulosic ester as described, for example, in PCT Pub. No WO 2013/019766 (Steelman et. al.), published Feb. 7, 2013, the disclosure of which is incorporated herein by reference.

An ink layer may be provided on at least one surface of the graphic film. In some embodiments, the ink layer creates a design. Imaging techniques suitable for imaging the film include ink jet printing, thermal mass transfer, flexography, dye sublimation, screen printing, electrostatic printing, offset printing, gravure printing, or other printing processes. Useful inks include piezo ink-jet inks, thermal transfer inks, ultraviolet curable inks, solvent based inks, and latex inks.

A top coat may also be employed as a functional layer. The top coat may be polymeric, and, for example, may be made of fluoropolymers, polyurethanes, polyvinylidene chloride (PVC), polycarbonates, or polyacrylics or copolymer thereof. A topcoat may be used to modify surface characteristics, but may also be used as a protective layer, for example, over an image. The topcoat may be a glass layer that protects a permanent graphic. This may be desirable for architectural, roofing, tiling, or similar applications.

The graphic film may also be treated with a conventional primer coating, and/or activated by flame or corona discharge, and/or by other surface treatment to enhance adhesion of a functional layer and/or adhesive layer thereto.

In some embodiments, the graphic film is a perforated laminate that includes a graphic film layer and a reflective layer behind the graphic film layer. For example, a white reflective layer or a silvered reflective layer may be used behind a perforated graphic layer. In some embodiments, the graphic film is a translucent laminate that includes a translucent graphic film layer and a partially reflective layer behind the translucent graphic film layer.

In some embodiments, solar energy devices described herein further comprise an ultraviolet light protective layer (UV-protective layer) on at least one surface of the visible light-transmitting reflector. In some embodiments, a UV-protective layer may be applied to both surfaces. A UV-protective layer typically shields the multilayer optical film from UV radiation that may cause degradation. In particular the ultraviolet radiation from 280 nm to 400 nm can induce degradation of plastics, which in turn results in color change and deterioration in mechanical properties Inhibition of photo-oxidative degradation is useful for outdoor applications wherein long term durability is desired. The absorption of UV light by polyethylene terephthalates, for example, starts at around 360 nm, increases markedly below 320 nm and is very pronounced at below 300 nm. In some embodiments, the ultraviolet light protective layer comprises poly (vinylidene difluoride), poly(methyl methacrylate), and an ultraviolet light absorber. Polyethylene naphthalates strongly absorb UV light in the 310-370 nm range, with an absorption tail extending to about 470 nm, and thus also benefits from blue light protection as described, for example, in U.S. patent application having Ser. No. 61/677,199, filed Jul. 30, 2012 (WO2014/022049—Publication date Feb. 6, 2014), the disclosure of which is incorporated herein by reference. Chain cleavage occurs in the presence of oxygen, and the predominant photooxidation products are carbon monoxide, carbon dioxide, and carboxylic acids. Besides the direct photolysis of the ester groups, consideration has to be given to oxidation reactions which likewise form carbon dioxide via peroxide radicals.

In some embodiments, the ultraviolet light protective layer is a multilayer ultraviolet light reflective mirror. In some embodiments, the multilayer ultraviolet light reflective mirror comprises UV absorbers as described in patent applications WO2011/062836 A1 (Hebrink et. al.), published May 26, 2011, and WO2010/078289 A1 (Hebrink et. al.), published Jul. 8, 2010, the disclosures of which are incorporated herein by reference.

Useful UV-protective layers may shield the multilayer optical film by reflecting UV light, absorbing UV light, scattering UV light, or a combination thereof. Useful UV protective layers may include a polymer or combination of polymers that is capable of withstanding UV radiation for an extended period of time while either reflecting, scattering, or absorbing UV radiation. Non-limiting examples of such polymers include poly(methylmethacrylate), silicone thermoplastics, fluoropolymers, and their copolymers, and blends thereof. An exemplary UV-protective layer comprises a blend of poly(methylmethacryate) and polyvinylidene difluoride.

A variety of optional additives may be incorporated into the UV protective layer to assist in its function of protecting the multilayer optical film. Non-limiting examples of the additives include one or more compounds selected from ultraviolet light absorbers, hindered amine light stabilizers, anti-oxidants, and combinations thereof.

UV stabilizers such as UV absorbers are chemical compounds which can intervene in the physical and chemical processes of photo-induced degradation. The photooxidation of polymers from UV radiation can therefore be prevented by use of a protective layer containing UV absorbers to effectively block UV light. UV absorbers are typically included in the UV-absorbing layer in an amount that absorb at least 70 percent (in some embodiments, at least 80 percent, 90 percent, or even at least 99 percent) of incident light in a wavelength region from 180 nm to 400 nm. UV absorbers may be red-shifted UV absorbers, which have enhanced spectral coverage in the long-wave UV region, enabling it to block the high wavelength UV light that can cause yellowing in polyesters. Typical UV-protective layer thicknesses are from 10 micrometers to 500 micrometers although thick and thinner UV-absorbing layers can be useful in some applications. Typically, the UV-absorber is present in the UV-absorbing layer in an amount of from 2 to 20 percent by weight, but lesser and greater levels may also be useful for some applications. In some embodiments, the ultraviolet light protective layer comprises poly(vinylidene difluoride), poly(methyl methacrylate), and an ultraviolet light absorber.

One exemplary UV absorber is a benzotriazole compound, 5-trifluoromethyl-2-(2-hydroxy-3-alpha-cumyl-5-tert-octylphenyl)-2H-benzotriazole. Other exemplary benzotriazoles include 2-(2-hydroxy-3,5-di-alpha-cumylphehyl)-2H-benzotriazole, 5-chloro-2-(2-hydroxy-3-tert-butyl-5-methylphenyl)-2H-benzotiazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-alpha-cumyl-5-tert-octylphenyl)-2H-benzotriazole, and 2-(3-tert-butyl-2-hydroxy-5-methylphenyl)-5-chloro-2H-benzotriazole. Additional exemplary UV absorbers include 2-(4,6-diphenyl-1,3,5-triazin-2-yl)-5-hexcyloxyphenol, and diphenyl triazine (available, for example, under the trade designation "TINUVIN 1600" from BASF, Florham Park, N.J., and those available from Ciba Specialty Chemicals Corp., Tarrytown, N.Y., under the trade designations "TINUVIN 1577" and "TINUVIN 900"). In addition, UV absorber(s) can be used in combination with hindered amine light stabilizer(s) (HALS) and/or antioxidants. Exemplary HALSs include those available from Ciba Specialty Chemicals Corp. under the trade designations "CHIMASSORB 944" and "TINUVIN 123". Exemplary antioxidants include those available under the trade designations "IRGANOX 1010" and "ULTRANOX 626" from Ciba Specialty Chemicals Corp.

Other additives may be included in the UV-absorbing layer. Small particle non-pigmentary zinc oxide and titanium oxide can also be used as blocking or scattering additives in the UV-absorbing layer. For example, certain nanometer-scale particles can be dispersed in polymer or coating substrates to minimize ultraviolet radiation degradation. The nanoparticles are transparent to visible light while either scattering or absorbing harmful UV radiation thereby reducing damage to thermoplastics. U.S. Pat. No. 5,504,134 (Palmer et al.), for example, describes attenuation of polymer substrate degradation due to ultraviolet radiation through the use of metal oxide particles in a size range of about 0.001 micrometer to about 0.20 micrometer in diameter (in some embodiments, from about 0.01 to about 0.15 micrometer) in diameter. U.S. Pat. No. 5,876,688 (Laundon), for example, describes a method for producing micronized zinc oxide particles that are small enough to be transparent when incorporated as UV blocking and/or scattering agents in paints, coatings, finishes, plastic articles, and cosmetics. These fine particles such as zinc oxide and titanium oxide with particle size ranged from 10 nm to 100 nm, which can attenuate UV radiation, are available, for example, from Kobo Products, Inc., South Plainfield, N.J. Flame retardants may also be incorporated as an additive in the UV-absorbing layer.

The thickness of the ultraviolet light protective layer is dependent upon an optical density target at specific wavelengths as calculated by the Beer-Lambert Law. In typical embodiments, the ultraviolet light absorbing layer has an optical density greater than 3.5 at 380 nm; greater than 1.7 at 390 nm; and greater than 0.5 at 400 nm. Those of ordinary skill in the art will recognize that the optical densities must remain fairly constant over the extended life of the article in order to provide the intended protective function.

In some embodiments, the ultraviolet light-protective layer is a multilayer ultraviolet light reflective mirror (multilayer UV-reflective mirror). The multilayer UV-reflective mirror is reflective to UV light; for example, it is at least 30 (in some embodiments, at least 40, 50, 60, 70, 80, 90, or even at least 95) percent reflective to at least a portion of UV light at a normal angle of incidence. The multilayer ultraviolet light reflective mirror is typically a multilayer optical film that reflects wavelengths of light from about 350 to about 400 nm (in some embodiments, 300 nm to 400 nm). In some embodiments, these wavelengths are included in the absorption bandwidth of the photovoltaic cell or solar thermal collector. The multilayer ultraviolet light reflective mirror can be made according to the techniques described above for making multilayer optical films except that the polymers for the layer pairs (e.g., third and fourth optical layers in some embodiments), layer thicknesses, and number of layers are selected to reflect UV light. The polymers that make the multilayer optical film are typically selected such that they do not absorb UV light in the 300 nm to 400 nm range. Exemplary suitable pairs of polymers useful for preparing multilayer UV reflective mirrors include polyethylene terephthalate with a tetrafluoroethylene, hexafluoropropylene, and vinylidene fluoride copolymer; poly(methyl methacrylate) with tetrafluoroethylene, hexafluoropropylene, and vinylidene fluoride copolymer; polyethylene terephthalate with SPDX; poly(methyl methacrylate) with SPDX; syndiotactic polystyrene with tetrafluoroethylene, hexafluoropropylene, and vinylidene fluoride copolymer; syndiotactic polystyrene with SPDX; modified polyolefin copolymers (e.g., EVA) with a tetrafluoroethylene, hexafluoropropylene, and vinylidene fluoride copolymer; a thermoplastic polyurethane with a tetrafluoroethylene, hexafluoropropylene, and vinylidene fluoride copolymer; and a thermoplastic polyurethane with SPDX. In some embodiments, a blend of tetrafluoroethylene, hexafluoropropylene, and vinylidene fluoride copolymer (available under the trade designation "DYNEON THV" (e.g., 220 grade or 2030 grade), from Dyneon LLC, Oakdale, Minn.) is employed with PMMA for multilayer UV mirrors reflecting 300-400 nm or with PET for multilayer mirrors reflecting 350-400 nm. In general, 100 to 1000 total layers of the polymer combinations are suitable for use with the present disclosure. Examples of multilayer UV light reflective mirrors can be found, for example, in Int. Pat. App. Pub. No. WO 2010/078105 (Hebrink et al.).

In some embodiments wherein the visible light-transmitting reflector comprises a multilayer UV-reflective mirror, the multilayer UV-reflective mirror comprises a UV absorber, including any of the UV absorbers described above. The UV absorber may be, for example, in one or more of the optical layers or in one or more non-optical skin layers on either side of the optical layer stack of the multilayer UV-reflective mirror.

While UV absorbers, HALS, nanoparticles, flame retardants, and anti-oxidants can be added to a UV protective layer, in other embodiments UV absorbers, HALS, nanoparticles, flame retardants, and anti-oxidants can be added to the multilayer optical layers themselves and/or optional non-optical skin layers or durable top coat layers. Fluorescing molecules and optical brighteners can also be added to a UV protective layer, the multilayer optical layers, an optional durable top coat layer, or a combination thereof.

In some embodiments, including embodiments in which the visible light-transmitting reflector includes a UV protective layer as described in any of the above embodiments, the visible light-transmitting reflector exhibits resistance to degradation by UV light. Resistance to degradation by UV light can be determined using the weathering cycle described in ASTM G155 (October 2005) and a D65 light source operated in the reflected mode. In some embodiments, under the noted test, the visible light-transmitting reflector does not change substantially in color, haze, or transmittance and does not significantly crack, peel, or delaminate. In some embodiments, after exposure of at least 18,700 kJ/m$^2$ at 340 nm, the b* value obtained using the CIE L*a*b* scale of the visible light-transmitting reflector increases by 10 or less (in some embodiments, 5 or less, 4 or less, 3 or less, or even 2 or less). In some embodiments, after exposure of at least 18,700 kJ/m$^2$ at 340 nm, the visible light-transmitting reflector exhibits a difference in haze versus the initial haze of up to 20 (in some embodiments, up to 15, 10, 5, 2, or even up to 1) percent. In some embodiments, after exposure of at least 18,700 kJ/m$^2$ at 340 nm, the visible light-transmitting reflector exhibits a difference in transmission versus the initial transmission of up to 20 (in some embodiments, up to 15, 10, 5, 2, or even up to 1) percent.

In some embodiments, including embodiments in which the visible light-transmitting reflector includes a UV-protective layer as described in any of the above embodiments (including embodiments where the UV-protective layer is a UV-reflective mirror, the visible light-transmitting reflector remains visible light-transmissive for at least a portion of the visible light spectrum. That is, the UV-protective layer is also at least partially visible light-transmissive.

In some embodiments, the visible light-transmitting reflector may include a layer including infrared absorbing particles to absorb at least some of the infrared light that is not reflected onto the photovoltaic cell. The infrared absorbing particles may be included in some of the optical layers or in non-optical skin layers, for example. The infrared radiation absorbing nanoparticles may include any material that preferentially absorbs infrared radiation. Examples of suitable materials include metal oxides such as tin, antimony, indium and zinc oxides and doped oxides. In some embodiments, the metal oxide nanoparticles include, tin oxide, antimony oxide, indium oxide, indium doped tin oxide, antimony doped indium tin oxide, antinomy tin oxide, antimony doped tin oxide or mixtures thereof. In some embodiments, the metal oxide nanoparticles include antimony oxide (ATO) and/or indium tin oxide (ITO). It may be useful to include infrared absorbing particles, for example, to prevent at least some of the non-reflected infrared light from entering a building or structure into which the solar energy device described herein is installed.

In some embodiments, the visible light-transmitting reflector includes tie layers, for example, to attach two multilayer optical films with different reflection bandwidths or to attach the multilayer optical film to the UV-protective layer in any of its embodiments. The optional tie layer may facilitate adhesion of the films and provide long term stability if the solar energy device described herein is exposed to outdoor elements in use.

The optional tie layer may be organic (e.g., a polymeric layer or adhesive), inorganic, or a combination thereof. Exemplary inorganic tie layers include amorphous silica, silicon monoxide, and metal oxides (e.g., tantalum pentoxide, titanium dioxide, and aluminum oxide). The tie layer may be provided by any suitable means, including vapor coating, solvent casting, and powder coating techniques. In some embodiments, the optional tie layer is typically substantially not absorptive of light (e.g., having an absorbance of less than 0.1 (in some embodiments, less than 0.01, 0.001, or even less than 0.0001)) over a wavelength range from 400 to 2494 nm. Useful adhesive tie layers include pressure-sensitive adhesives, thermosetting adhesives, hot melt adhesives, and combinations thereof. Exemplary useful adhesive tie layers include optically clear acrylic pressure sensitive adhesives (25 micrometer thickness) available from 3M Company, St. Paul, Minn., under the trade designations "OPTICALLY CLEAR LAMINATING ADHESIVE 8141," and "OPTICALLY CLEAR LAMINATING ADHESIVE 8171"; tackified adhesives as described in U.S. Pat. No. 7,371,464 B2 (Sherman et al.); and non-silicone pressure-sensitive adhesives as described, for example, in U.S. Pat. Appl. Pub. No. 2011/0123800 (Sherman et al.). Further examples of tie layers include polydiorganosiloxane polyoxamide (PDX), CoPETs including modifications such as with functional groups sulfonic acids, polymethylmethacrylate/polyvinylidenefluoride (PMMA/PVDF) blends, modified olefins with functional comonomers such as maleic anhydride, acrylic acid, methacrylic acid or vinyl acetate. Additionally, UV or thermally curable acrylates, silicones, epoxies, siloxanes, urethane acrylates may be suitable as tie layers. The tie layers may optionally contain UV absorbers as described above and may optionally contain conventional plasticizers, tackifiers, or combinations thereof. The tie layer may be applied utilizing conventional film forming techniques. Since the tie layers are part of the visible light-transmitting reflector, the tie layers are at least partially transmissive to visible light.

In some embodiments, the visible light transmitting reflector includes a durable top coat to assist in preventing the premature degradation of the solar concentrating mirror due to exposure to outdoor elements. The durable topcoat is typically abrasion and impact resistant and does not interfere with the reflection of a selected bandwidth of light corresponding to the absorption bandwidth of the photovoltaic cell or solar thermal collector nor the transmission of visible light. Durable top coat layers may include one or more of the following non-limiting examples, PMMA/PVDF blends, thermoplastic polyurethanes, curable polyurethanes, CoPET, cyclic olefin copolymers (COC's), fluoropolymers and their copolymers such as polyvinylidene fluoride (PVDF), polyethylene tetrafluoroethylene (ETFE), polyethylene hexafluoropropylene (FEP), and copolymers derived from tetrafluoroethylene, hexafluoropropylene, and vinylidene fluoride (THV), thermoplastic and curable acrylates, cross-linked acrylates, cross-linked urethane acrylates, cross-linked urethanes, curable or cross-linked polyepoxides, and polydimethylsiloxane oxamide copolymer (SPDX). Strippable polypropylene copolymer skins may also be employed. Alternatively, silane silica sol copolymer hard coating can be applied as a durable top coat to improve scratch resistance. The durable top coat may contain UV absorbers, hindered amine light stabilizers HALS, and antioxidants as described above. The visible light-transmitting reflector coated with such a durable top coat is typically thermoformable before the top coat is fully cured at an elevated temperature. The cure temperature depends on the selected materials but may be, for example, 80° C. for 15 minutes to 30 minutes.

A variety of methods may be useful for evaluating the impact or abrasion resistance of the durable top coat. Taber abrasion is one test to determine a film's resistance to abrasion, and resistance to abrasion is defined as the ability of a material to withstand mechanical action such as rubbing, scrapping, or erosion. According to the ASTM D1044 (2008) test method, a 500-gram load is placed on top of CS-10 abrader wheel and allowed to spin for 50 revolutions on a 4 square inch test specimen. The reflectivity of the sample before and after the Taber abrasion test is measured, and results are expressed by changes in % reflectivity. In some embodiments, change in % reflectivity is expected to be less than 20% (in some embodiments, less than 10%, or even less than 5%). Other suitable tests for mechanical durability include break elongation, pencil hardness, sand blast test, and sand shaking abrasion. The durable top coat may also enhance the resistance to weathering of the visible light-transmitting reflector, which may be evaluated by ASTM G155 (October 2005) as described above.

In some embodiments, the multilayer optical film is formed into multiple reflective surfaces that reflect onto multiple photovoltaic cells or solar thermal collectors.

In some embodiments, the multilayer optical film is present in multiple parallel ridges separated by multiple land areas, and wherein multiple photovoltaic cells or solar thermal collectors are located in the multiple land areas. In some embodiments, each land area has a single row of photovoltaic cells or solar thermal collectors (see FIGS. 1A, 2, and 3).

In some embodiments, solar energy devices described herein further comprise multiple parallel ridges each having first and second opposing ridge faces, wherein the visible light-transmitting reflector is located on each first ridge face, and wherein the photovoltaic cell or solar thermal collector is located on each second ridge face. In some embodiments, the photovoltaic cell or solar thermal collector on the second ridge face are present as a single row of photovoltaic cells or solar thermal collectors (see FIGS. 1A, 2, and 3).

In some embodiments, solar energy devices described herein further comprise parabolic shaped visible light transmitting mirrors shaped to concentrate solar energy onto a single row of photovoltaic cells or a solar thermal absorbing tube.

In some embodiments, solar energy devices described herein further comprise truncated compound parabolic concentrator shaped visible light transmitting mirrors shaped to concentrate solar energy onto a single row of photovoltaic cells or solar thermal absorber.

In some embodiments, the visible light-transmitting reflector comprises an antisoiling coating. Examples of antisoiling components include fluoropolymers, silicone polymers, titanium dioxide particles, polyhedral oligomeric silsesquioxanes (e.g., as available as polyhedral oligomeric silsesquioxanes (POSS) from Hybrid Plastics of Hattiesburg, Miss.), and combinations thereof. In some embodiments, the antisoiling coating may be a hydrophobic coating which includes a polymer matrix (e.g., a silicone or fluoropolymer) and nanoparticles dispersed therein. The nanoparticles may be, for example, polymer (e.g., fluoropolymer) particles, particles of a dielectric material (e.g., silica, alumina, zirconia, titania, or indium tin oxide particles), or metal (e.g., gold) particles. Further details regarding such hydrophobic coatings are described, for example, in Int. Pat. Appl. Pub. Nos. 2012/058090 (Zhang et al.) and 2012/058086 (Zhang et al.), the disclosures of which are incorporated by reference herein. In some embodiments, the antisoiling coating may comprise nanosilica and may be coated out of water. Further details of such coatings are described in Int. Pat. Appl. Pub. Nos. 2012/047867 (Brown et al.) and 2012/047877 (Brown et al.), the disclosures of which are incorporated by reference herein.

In some embodiments, the visible light-transmitting reflector comprises a scratch-resistant coating. Optionally a hardcoat can be provided by techniques known in the art, including those described in U.S. Pat. No 7,153,588 (McMan) and application having U.S. Ser. No. 61/614,297 (Clear et al.) (WO2013/142239 Published Sep. 26, 2013), the disclosures of which are incorporated herein by reference. Additional hard coats include silica filled siloxanes available, for example, from California Hard Coat, San Diego, Calif., under the trade designation "PERMANEW", and from Momentive, Columbus, Ohio, under the trade designations "AS4000" and "AS4700." Exemplary acrylic UV protective hardcoats are available, for example, under the trade designations "UVT610 (GEN IV)" and "UVT200" from Red Spot Paint & Varnish Company, Evansville, Ind. Exemplary UV protective acrylic hard coats are disclosed, for example, in application having U.S. Ser. No. 61/614,297, filed Mar. 22, 2012, (WO2013/142239 Published Sep. 26, 2013). Use of hardcoats can, for example, reduce or prevent premature degradation of the article due to exposure to outdoor elements. The hardcoat is generally abrasion and impact resistant and does not interfere with the primary function of reflecting a selected bandwidth of electromagnetic radiation.

In some embodiments, solar energy devices described herein further comprises a visible light-transmitting substrate. The multilayer optical film may be applied to the substrate and optionally the photovoltaic cell or solar thermal collector may be positioned on a substrate. Although, in some applications, a substrate is not necessary, applying the solar energy device described herein onto a substrate may provide additional rigidity or dimensional stability, which may be useful, for example, when the solar energy device is installed as part of a building or other structure. Suitable substrates include glass sheets, polymeric sheets, polymer fiber composites, and glass fiber composites. An optional tie layer, such as any of those previously described, may be employed in bonding the solar energy devices to the substrate. Also, optionally a UV absorber, such as any of those previously described, may be included in the substrate. One exemplary substrate material is twin wall polycarbonate sheeting (available, for example, under the trade designation "SUNLITE MULTIWALL POLYCARBONATE SHEET" from Palram Americas, Inc., Kutztown, Pa.). In other embodiments, the solar energy device may be sandwiched between two layers of acrylic sheeting (available, for example, under the trade designation "PLEXIGLAS" from Arkema, Inc., Philadelphia, Pa.).

Although the substrate onto which at least the visible light-transmitting reflector is applied should let visible light through, it need not be completely transparent. The substrate and the multilayer optical film that form the visible light-transmitting reflector may also be translucent and still allow visible light into a building or other structure, for example. However, the substrate should not be provided with any coating or sheeting that would destroy the visible light-transmitting properties of the reflector. For example, no opaque white, black, or metallic film or paint should be applied on the substrate or the multilayer optical film of the visible light-transmitting reflector.

The visible light-transmitting reflector, and therefore any portion thereof, is typically compliant, which means that the visible light-transmitting reflector is dimensionally stable but pliable enough to enable molding or shaping into various forms. In some embodiments, the materials selected for the visible light-transmitting reflector have less than 10% by weight film formers (crosslinking agents or other multifunctional monomers), based on the total weight of the materials.

Solar energy devices described herein may be designed to have a variety of sizes, shapes, and configurations of the photovoltaic cell or solar thermal collector and the visible light-transmitting reflector depending on the desired application. In some embodiments, the visible light-transmitting reflector comprises a multilayer optical film formed into multiple reflective surfaces that reflect onto multiple photovoltaic cells or solar thermal collectors. For example, the visible light-transmitting reflector may be formed into shapes or dimensions conventionally used for solar concentrators (e.g., troughs or parabolic dishes). In some of these embodiments, the multilayer optical film is thermoformed. Thermoforming is generally described in U.S. Pat. No. 6,788,463 (Merrill et al.), herein incorporated by reference in its entirety. The multiple photovoltaic cells or solar thermal collectors and multiple reflective surfaces can be arranged in a variety of ways. Thermoformed polymeric designs are lightweight and when designed with a low profile can eliminate the need for expensive photovoltaic racking.

Solar energy devices described herein can be used, for example, a sign (e.g., an advertising sign or a traffic sign), on the side and/or roof, as well as in a window, of a building. The solar energy device may be installed, for example, as part of a building and allow visibility of the graphic film or lighted display positioned closer to the second major surface of the visible light transmitting reflector.

In some embodiments of solar energy device described herein, the power output of the photovoltaic cell or solar thermal collector is increased by at least 10 (in some embodiments, at least 15, 20, or even at least 25) percent in comparison to an equivalent photovoltaic cell or a solar thermal collector, as applicable, in the absence of any visible light transmitting mirrors.

Exemplary Embodiments

1A. A solar energy device comprising:
  at least one of a photovoltaic cell or a solar thermal collector having an absorption bandwidth that includes at least a portion of the near infrared wavelength region of the solar spectrum (i.e., at least a portion in a range from 800 nm to 1200 nm);
  a visible light-transmitting reflector having first and second generally opposed major surfaces, the visible light-transmitting reflector positioned to reflect light from the first major surface onto the at least one of a photovoltaic cell or a solar thermal collector, the visible light-transmitting reflector comprising a multilayer optical film having an optical stack comprising a plurality of alternating first and second optical layers with different indices of refraction, wherein the multilayer optical film reflects at least a portion of light in a range of wavelengths that corresponds with the absorption bandwidth of the at least one of a photovoltaic cell or a solar thermal collector; and
  at least one of a graphic film (in some embodiments, a partially transmissive graphic film) or lighted display positioned closer to the second major surface of the visible light-transmitting reflector than to the first major surface of the visible light-transmitting reflector, wherein the graphic film or a lighted display present is visible through the visible light-transmitting reflector.

2A. The solar energy device of Exemplary Embodiment 1A comprising the lighted display.

3A. The solar energy device of any preceding Exemplary Embodiment A comprising the graphic film.

4A. The solar energy device of any Exemplary Embodiment A, wherein the graphic film is a partially transmissive graphic film.

5A. The solar energy device of any preceding Exemplary Embodiment A, wherein the solar energy device is installed as part of a building and allows visibility of the graphic film or lighted display positioned closer to the second major surface of the visible light transmitting reflector.

6A. The solar energy device of any preceding Exemplary Embodiment A, wherein the visible light-transmitting reflector has an average visible light transmission of at least 30 percent.

7A. The solar energy device of any preceding Exemplary Embodiment A, wherein the multilayer optical film is a visible light transmitting reflector having a left band edge in a range from 600 nanometers to 1000 nanometers.

8A. The solar energy device of any preceding Exemplary Embodiment A, wherein the multilayer optical film has an average light reflection of at least 50 percent at a normal angle to the multilayer optical film in a wavelength range selected from the group consisting of 650 nanometers to 1350 nanometers, 650 nanometers to 1500 nanometers, 850 nanometers to 1200 nanometers, and 850 nanometers to 1500 nanometers.

9A. The solar energy device of any preceding Exemplary Embodiment A, further comprising an ultraviolet light protective layer on at least one surface of the visible light-transmitting reflector.

10A. The solar energy device of Exemplary Embodiment 9A, wherein the ultraviolet light protective layer comprises poly(vinylidene difluoride), poly(methyl methacrylate), and an ultraviolet light absorber.

11A. The solar energy device of Exemplary Embodiment 9A or 10A, wherein the ultraviolet light protective layer is a multilayer ultraviolet light reflective mirror.

12A. The solar energy device of Exemplary Embodiment 11A, wherein the multilayer ultraviolet light reflective mirror comprises UV absorbers.

13A. The solar energy device of any preceding Exemplary Embodiment A, further comprising a visible light-transmitting substrate to which at least the multilayer optical film is applied.

14A. The solar energy device of any preceding Exemplary Embodiment A, wherein the multilayer optical film is formed into multiple reflective surfaces that reflect onto multiple photovoltaic cells or solar thermal collectors.

15A. The solar energy device of any preceding Exemplary Embodiment A, wherein the multilayer optical film is present in multiple parallel ridges separated by multiple land areas, and wherein multiple photovoltaic cells or solar thermal collectors are located in the multiple land areas.

16A. The solar energy device of Exemplary Embodiment 15A, wherein each land areas has a single row of photovoltaic cells or solar thermal collectors.

17A. The solar energy device of any of preceding Exemplary Embodiment A, further comprising multiple parallel ridges each having first and second opposing ridge faces, wherein the visible light-transmitting reflector is located on each first ridge face, and wherein the at least one of a photovoltaic cell or a solar thermal collector is located on each second ridge face.

18A. The solar energy device of Exemplary Embodiment 17A, wherein the at least one of a photovoltaic cell or a solar thermal collector on the second ridge face are present as a single row of photovoltaic cells or solar thermal collectors, as applicable.

19A. The solar energy device of any preceding Exemplary Embodiment A, further comprising a visible light transmitting reflector having a parabolic shape.

20A. The solar energy device of any preceding Exemplary Embodiment A, further comprising a visible light transmitting reflector having a truncated compound parabolic shape.

21A. The solar energy device of any preceding Exemplary Embodiment A, further comprising at least one of an anti-soiling or a scratch-resistant coating on at least one surface of the visible light-transmitting reflector.

22A. The solar energy device of any preceding Exemplary Embodiment A, wherein the power output of the at least one of a photovoltaic cell or a solar thermal collector is increased by at least 10 (in some embodiments, at least 15, 20, or even at least 25) percent in comparison to an equivalent photovoltaic cell or solar thermal collector, as applicable, in the absence of any visible light transmitting mirrors.

23A. The solar energy device of any preceding Exemplary Embodiment A comprising the graphic film.

24A. The solar energy device of any of Exemplary Embodiments 1A to 22A comprising the lighted display.

25A. The solar energy device of any Exemplary Embodiment 24A, wherein the lighted display is a liquid crystal display.

26A. The solar energy device of any preceding Exemplary Embodiment A comprising the photovoltaic cell.

27A. The solar energy device of Exemplary Embodiment 26A, wherein the photovoltaic cell is one of a crystalline silicon single junction cell, a ribbon silicon cell, an amorphous silicon photovoltaic cell, a copper indium gallium selenide cell, a cadmium telluride photovoltaic cell, an organic photovoltaic cell, or a gallium arsenide cell.

28A. The solar energy device of any of Exemplary Embodiments 1A to 25A comprising the solar thermal collector.

29A. A sign comprising the solar energy device of any preceding Exemplary Embodiment A used as a sign for advertising.

30A. The sign of Exemplary Embodiment 29A that is an advertising sign.

31A. The sign of Exemplary Embodiment 29A that is a traffic sign.

32A. A roof of a building, wherein the roof comprises the solar energy device of any of Exemplary Embodiments 1A to 28A.

33A. A side of a building comprising the solar energy device of any of Exemplary Embodiments 1A to 28A.

34A. A window comprising the solar energy device of any of Exemplary Embodiments 1A to 28A.

1B. A solar energy device comprising:
  at least one of a photovoltaic cell or a solar thermal collector having an absorption bandwidth that includes at least a portion of the near infrared wavelength region of the solar spectrum (i.e., at least a portion in a range from 800 nm to 1200 nm);
  a visible light-transmitting reflector having first and second generally opposed major surfaces, the visible light-transmitting reflector positioned to reflect light from the first major surface onto the at least one of a photovoltaic cell or a solar thermal collector, the visible light-transmitting reflector comprising a multilayer optical film having an optical stack comprising a plurality of alternating first and second optical layers with different indices of refraction, wherein the multilayer optical film reflects at least a portion of light in a range of wavelengths that corresponds with the absorption bandwidth of the at least one of a photovoltaic cell or a solar thermal collector; and
  a partially transmissive graphic film positioned closer to the first major surface of the visible light-transmitting reflector than to the second major surface of the visible light-transmitting reflector, wherein infrared light passes through the partially transmissive graphic film.

2B. The solar energy device of any preceding Exemplary Embodiment B, wherein the visible light-transmitting reflector has an average visible light transmission of at least 30 percent.

3B. The solar energy device of any preceding Exemplary Embodiment B, wherein the multilayer optical film is a visible light transmitting reflector having a left band edge in a range from 600 nanometers to 1000 nanometers.

4B. The solar energy device of any preceding Exemplary Embodiment B, wherein the multilayer optical film has an average light reflection of at least 50 percent at a normal angle to the multilayer optical film in a wavelength range selected from the group consisting of 650 nanometers to 1350 nanometers, 650 nanometers to 1500 nanometers, 850 nanometers to 1200 nanometers, and 850 nanometers to 1500 nanometers.

5B. The solar energy device of any preceding Exemplary Embodiment B, further comprising an ultraviolet light protective layer on at least one surface of the visible light-transmitting reflector.

6B. The solar energy device of Exemplary Embodiment 5B, wherein the ultraviolet light protective layer comprises poly(vinylidene difluoride), poly(methyl methacrylate), and an ultraviolet light absorber.

7B. The solar energy device of Exemplary Embodiment 5B or 6B, wherein the ultraviolet light protective layer is a multilayer ultraviolet light reflective mirror.

8B. The solar energy device of Exemplary Embodiment 7B, wherein the multilayer ultraviolet light reflective mirror comprises UV absorbers.

9B. The solar energy device of any preceding Exemplary Embodiment B, further comprising a visible light-transmitting substrate to which at least the multilayer optical film is applied.

10B. The solar energy device of any preceding Exemplary Embodiment B, wherein the multilayer optical film is formed into multiple reflective surfaces that reflect onto multiple photovoltaic cells or solar thermal collectors.

11B. The solar energy device of any preceding Exemplary Embodiment B, wherein the multilayer optical film is present in multiple parallel ridges separated by multiple land areas, and wherein multiple photovoltaic cells or solar thermal collectors are located in the multiple land areas.

12B. The solar energy device of Exemplary Embodiment 11B, wherein each land areas has a single row of photovoltaic cells or solar thermal collectors.

13B. The solar energy device of any of preceding Exemplary Embodiment B, further comprising multiple parallel ridges each having first and second opposing ridge faces, wherein the visible light-transmitting reflector is located on each first ridge face, and wherein the at least one of a photovoltaic cell or a solar thermal collector is located on each second ridge face.

14B. The solar energy device of Exemplary Embodiment 13B, wherein the at least one of a photovoltaic cell or a solar thermal collector on the second ridge face are present as a single row of photovoltaic cells or solar thermal collectors, as applicable.

15B. The solar energy device of any preceding Exemplary Embodiment B, further comprising a visible light transmitting reflector having a parabolic shape.

16B. The solar energy device of any preceding Exemplary Embodiment B, further comprising a visible light transmitting reflector having a truncated compound parabolic shape.

17B. The solar energy device of any preceding Exemplary Embodiment B, further comprising at least one of an anti-soiling or a scratch-resistant coating on at least one surface of the visible light-transmitting reflector.

18B. The solar energy device of any preceding Exemplary Embodiment B, wherein the power output of the at least one of a photovoltaic cell or a solar thermal collector is increased by at least 10 (in some embodiments, at least 15, 20, or even at least 25) percent in comparison to an equivalent photovoltaic cell or solar thermal collector, as applicable, in the absence of any visible light transmitting mirrors.

19B. The solar energy device of any preceding Exemplary Embodiment B comprising the graphic film.

20B. The solar energy device of any of Exemplary Embodiments 1B to 18B comprising the lighted display.

21B. The solar energy device of any Exemplary Embodiment 20B, wherein the lighted display is a liquid crystal display.

22B. The solar energy device of any preceding Exemplary Embodiment B comprising the photovoltaic cell.

23B. The solar energy device of Exemplary Embodiment 22B, wherein the photovoltaic cell is one of a crystalline silicon single junction cell, a ribbon silicon cell, an amorphous silicon photovoltaic cell, a copper indium gallium selenide cell, a cadmium telluride photovoltaic cell, an organic photovoltaic cell, or a gallium arsenide cell.

24B. The solar energy device of any of Exemplary Embodiments 1B to 21B comprising the solar thermal collector.

25B. A sign comprising the solar energy device of any preceding Exemplary Embodiment B used as a sign for advertising.

26B. The sign of Exemplary Embodiment 25B that is an advertising sign.

27B. The sign of Exemplary Embodiment 25B that is a traffic sign.

28B. A roof of a building, wherein the roof comprises the solar energy device of any of Exemplary Embodiments 1B to 24B.

29B. A side of a building comprising the solar energy device of any of Exemplary Embodiments 1B to 24B.

30B. A window comprising the solar energy device of any of Exemplary Embodiments 1B to 24B.

Foreseeable modifications and alterations of this disclosure will be apparent to those skilled in the art without departing from the scope and spirit of this invention. This invention should not be restricted to the embodiments that are set forth in this application for illustrative purposes.

What is claimed is:

1. A solar energy device comprising:
   at least one of a photovoltaic cell or a solar thermal collector having an absorption bandwidth that includes at least a portion of the near infrared wavelength region of the solar spectrum;
   a visible light-transmitting reflector having first and second generally opposed major surfaces, the visible light-transmitting reflector positioned to reflect light from the first major surface onto the at least one of a photovoltaic cell or a solar thermal collector, the visible light-transmitting reflector comprising a multilayer optical film having an optical stack comprising a plurality of alternating first and second optical layers with different indices of refraction, wherein the multilayer optical film reflects at least a portion of light in a range of wavelengths that corresponds with the absorption bandwidth of the at least one of a photovoltaic cell or a solar thermal collector; and
   at least one graphic film positioned closer to the second major surface of the visible light-transmitting reflector than to the first major surface of the visible light-transmitting reflector, wherein the graphic film is visible through the visible light-transmitting reflector and includes at least one of a pattern or image.

2. The solar energy device of claim 1, wherein the graphic film is a partially transmissive graphic film.

3. The solar energy device of claim 1, wherein the solar energy device is installed as part of a building and allows visibility of the graphic film positioned closer to the second major surface of the visible light transmitting reflector.

4. The solar energy device of claim 1, wherein the visible light-transmitting reflector has an average visible light transmission of at least 30 percent.

5. The solar energy device of claim 1, wherein the multilayer optical film is a visible light transmitting reflector having a left band edge in a range from 600 nanometers to 1000 nanometers.

6. The solar energy device of claim 1, wherein the multilayer optical film has an average light reflection of at least 50 percent at a normal angle to the multilayer optical film in a wavelength range selected from the group consisting of 650 nanometers to 1350 nanometers, 650 nanometers to 1500 nanometers, 850 nanometers to 1200 nanometers, and 850 nanometers to 1500 nanometers.

7. The solar energy device of claim 1, further comprising multiple parallel ridges each having first and second opposing ridge faces, wherein the visible light-transmitting reflector is located on each first ridge face, and wherein the at least one of a photovoltaic cell or a solar thermal collector is located on each second ridge face.

8. The solar energy device of claim 7, wherein the at least one of a photovoltaic cell or a solar thermal collector on the second ridge face are present as a single row of photovoltaic cells or solar thermal collectors, as applicable.

* * * * *